United States Patent [19]

Barlow et al.

[11] 4,266,556

[45] May 12, 1981

[54] ELECTRICALLY HEATED SWEAT COLLECTION DEVICE AND METHOD

[75] Inventors: Wayne K. Barlow; Wallace A. Gibbons, both of Logan, Utah

[73] Assignee: Wescor, Inc., Logan, Utah

[21] Appl. No.: 955,093

[22] Filed: Oct. 26, 1978

[51] Int. Cl.³ ............................................. A61B 19/00
[52] U.S. Cl. .................................. 128/760; 128/303.1; 128/399; 128/630
[58] Field of Search ................. 128/630, 734, 632–635, 128/742, 760, 399, 303.1, 24.1; 219/228, 241

[56] References Cited

U.S. PATENT DOCUMENTS

| | | | |
|---|---|---|---|
| 2,837,084 | 6/1958 | Brumek | 128/24.1 |
| 3,327,713 | 6/1967 | Eidus | 128/399 |
| 3,516,411 | 6/1970 | Adler | 128/24.1 X |
| 3,635,213 | 1/1972 | Lahay | 128/632 |
| 3,794,910 | 2/1974 | Ninke et al. | 128/760 X |
| 4,005,700 | 2/1977 | Parker | 128/632 |
| 4,041,276 | 8/1977 | Schwarz et al. | 219/501 X |
| 4,041,932 | 8/1977 | Fostick | 128/633 |

OTHER PUBLICATIONS

Phillips, W. R., *Pediatrics*, 1963, Jul., pp. 89–92.
Webster, L. et al., *Med. Journ. of Australia*, Jun. 18, 1977, pp. 923–927.

*Primary Examiner*—Kyle L. Howell
*Attorney, Agent, or Firm*—Mallinckrodt & Mallinckrodt

[57] ABSTRACT

A sweat collection device for use with equipment for inducing human sweat has an electrically heated cup member whose temperature is maintained substantially constant by monitoring the temperature of the cup and controlling the electrical power supplied thereto in accordance with requirements determined by the temperature monitoring.

8 Claims, 5 Drawing Figures

ELECTRICALLY HEATED SWEAT COLLECTION DEVICE AND METHOD

BACKGROUND OF THE INVENTION

1. Field

The invention is in the field of sweat collection apparatus, whereby human sweat is collected for later medical evaluation and analysis.

2. State of the Art

It is desirable in some circumstances to collect samples of sweat from a human and perform tests on the sweat for medical purposes. For example, it was discovered in the 1950's that children with cystic fibrosis had elevated levels of chloride in their sweat. It has now become a routine way of screening children for cystic fibrosis to collect a sample of sweat for measurement of chloride ion levels. Such measurement may be accomplished by a chloride assay, electrical conductivity measurement, or by vapor-pressure osmolality measurements of the sweat sample.

Samples of sweat may be collected in various ways. The most common method used today is to introduce pilocarpine nitrate into the skin by means of an electrical current flowing through the skin between a pair of electrodes attached to the skin. This process is called Iontophoresis. Generally, current flow is continued for about 15 minutes, after which the electrodes are removed and a collection cup is placed over the area of the skin where the pilocarpine nitrate has been administered. After approximately 15 minutes, the sweat that has formed on the skin under the cup is collected into the cup by scraping the cup across the skin. Normally the collection cup is at room temperature which is a temperature below normal body and skin temperature.

The July, 1963 issue of Pediatrics contained an article by William R. Phillips, M.D. entitled "Electrical Conductivity of Sweat, A Simple, Home-Assembled Apparatus". In the section of the article entitled "Technique", Dr. Phillips says "A 75-watt lamp is placed 6 or 8 inches from the cup to keep it warm during the collection period. This heat prevents condensation of salt free moisture on the walls of the cup. It also increases the yield."

In the June 18, 1977 issue of the Medical Journal of Australia, an article by Lewis Webster, Ph.D. and Helen Lochlin entitled "Cystic Fibrosis Screening by Sweat Analysis, A Critical Review of Techniques", discusses the problem of condensate error which affects the reliability of sweat measurements and says "the condensate error, which has been noted elsewhere, could be minimized by arranging that the inverted cup be heated to a higher temperature than the skin surface throughout the collection period." The article goes on to say that the use of heat lamps is not practical on a large scale or for use with neonates, and then says "Extensive trials were undertaken to design the cup shown in FIG. 1, of convenient size and simple to construct, which could be preheated to a degree which maintained an optimal temperature differential during collection." The cup developed is then described. Basically, the cup has a heat reservoir of brass which is preheated before use and can maintain the cup at a temperature above skin temperature during time of collection, or about 15 minutes.

The cup developed by Webster and Lochlin has the inherent problem that only so much heat can be stored in the heat reservoir and that the cup at the beginning of the collection period has to be at a temperature which is uncomfortably high for many people in order that enough heat is stored so that the sweat collection is completed before the temperature of the cup falls below skin temperature. This gives a maximum collection time of about 15 minutes in most cases. Further, the temperature is not held constant or otherwise controlled during sweat collection. This is also true when heat lamps are used. There is no real temperature control. Thus, there remains much room for improving the collection cup.

SUMMARY OF THE INVENTION

According to the invention, a sweat collection device for use with equipment for inducing sweat has a cup member that is electrically heated and in which the temperature of the cup is maintained substantially constant by temperature monitoring and controlling supply of electrical power to the cup in accordance with the requirements determined by the temperature monitoring.

The cup member is made of a heat conductive material, such as aluminum, and has a heating element and temperature sensor attached thereto, preferably in intimate heat transfer relationship with the bottom of the cup. Means are provided to supply power to the heating element in accordance with requirements determined as a result of temperature data obtained by the temperature sensor.

THE DRAWINGS

In the accompanying drawings, which represent the best mode presently contemplated of carrying out the invention:

FIG. 1 is a pictorial view of a sweat collection device of the invention looking into the cup member;

FIG. 2, a pictorial view of the same, turned bottom up and wherein an encapsulating boot is removed to reveal heating and temperature sensing elements, the view being drawn to a larger scale;

FIG. 3, a vertical section taken on the line 3—3 of FIG. 2;

FIG. 4, a circuit diagram of the temperature sensing and heater control system; and FIG. 5, a circuit diagram of the electrical power supply system.

DETAILED DESCRIPTION OF THE ILLUSTRATED EMBODIMENT

Figure 1:
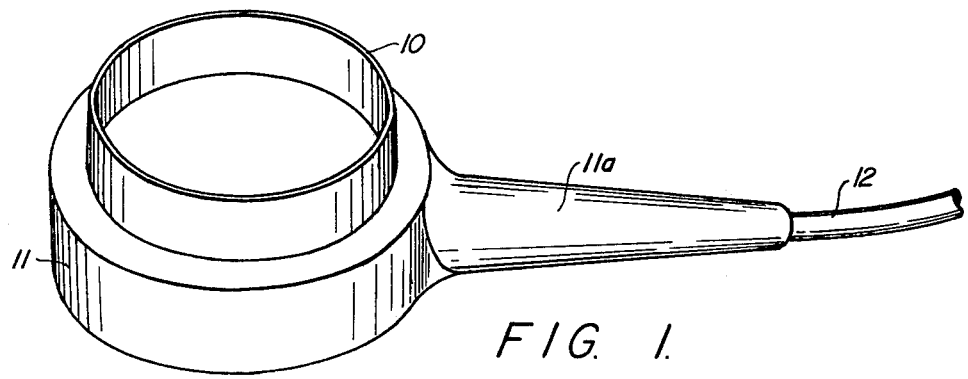

As illustrated, a cup member 10 for placing against the skin of a patient from whom sweat is to be collected is made of a heat conductive material, preferably aluminum, and has its bottom portion (to which are attached heating and sensing elements) completely encapsulated in a molded boot 11 of an elastomer material. An electrical cord 12 containing several conductors 13, 14, 15, 16, and 17, FIG. 2, extends from boot 11 to the location of temperature sensing and heater control circuitry through a handle member 11a which is advantageously molded integrally with boot 11.

Figure 2:
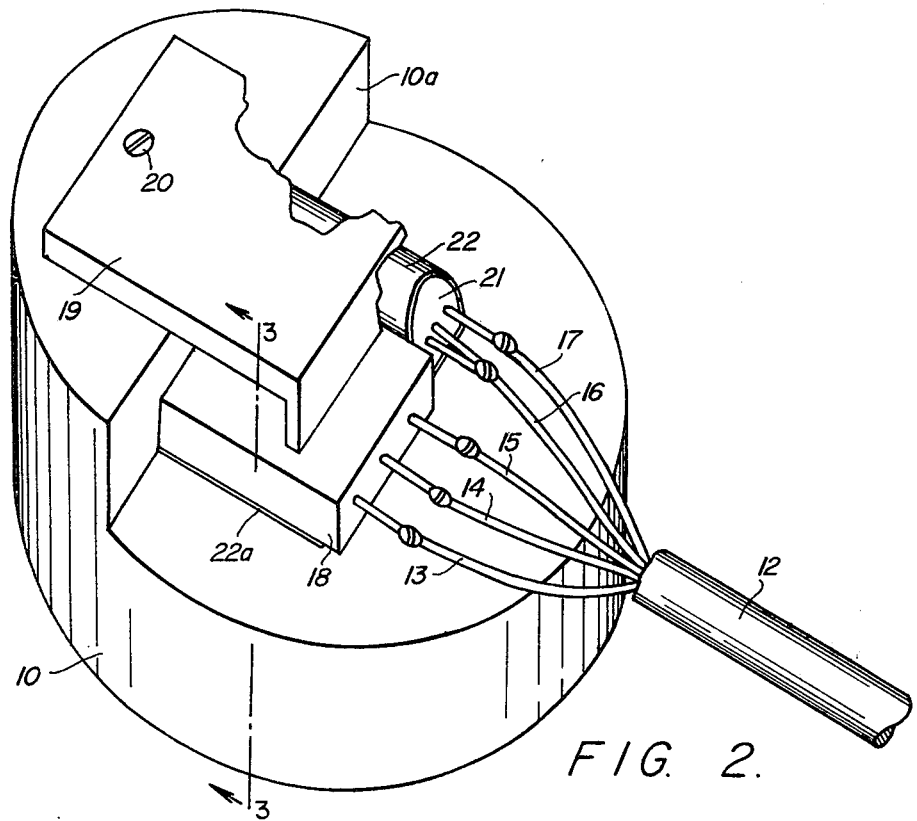
Figure 3:
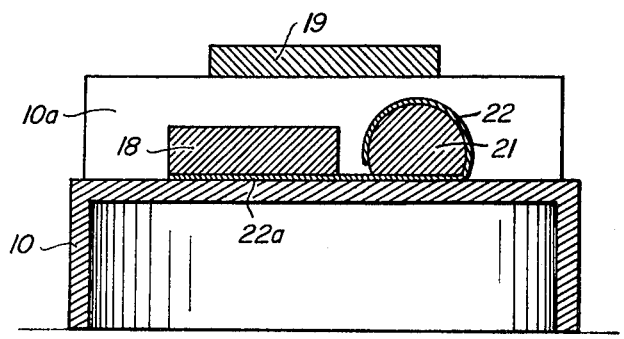

FIGS. 2 and 3 show cup 10 with the encapsulating boot 11 and handle member 11a removed. A heating element 18 is held in place against the bottom of cup 10 by a retaining piece 19 also advantageously of aluminum which is attached to a bottom extension 10a of cup 10, as by a screw 20. A temperature sensor 21 is also held in place against the bottom of cup 10 by the same retaining piece 19.

While various types of heating elements and temperature sensors may be used, it has been found that a commercial transistor, such as a National Semiconductor 2N6037, may be used as a heating element and that another commercial transistor, such as an RCA SK3137, may be used as a temperature sensor.

A preferred physical arrangement of the heating transistor and of the sensing transistor is shown in FIG. 3, wherein the temperature sensing transistor 21 is placed in a heat sink 22, also advantageously of aluminum, which encircles transistor 21 and extends outwardly at one side as a flat tab or pad portion 22a, FIG. 3. Such flat tab portion 22a is sandwiched between the bottom of cup 10 and heating transistor 18 in contact with both. Silicon grease is desirably used on all contacting surfaces to improve heat transfer. Electrical conductors 13, 14, and 15 powering heating transistor 18 and electrical conductors 16 and 17 powering temperature sensing transistor 21 are grouped together in electrical cord 12 which passes through handle 11a into the vicinity of control circuitry for the transistors, where the several conductors make appropriate electrical connections, respectively, with such control circuitry. Encapsulating boot 11 and its handle extension 11a surround the lower portion of cup 10 and cord 12, respectively, and protect the electrical connections.

Figure 4:
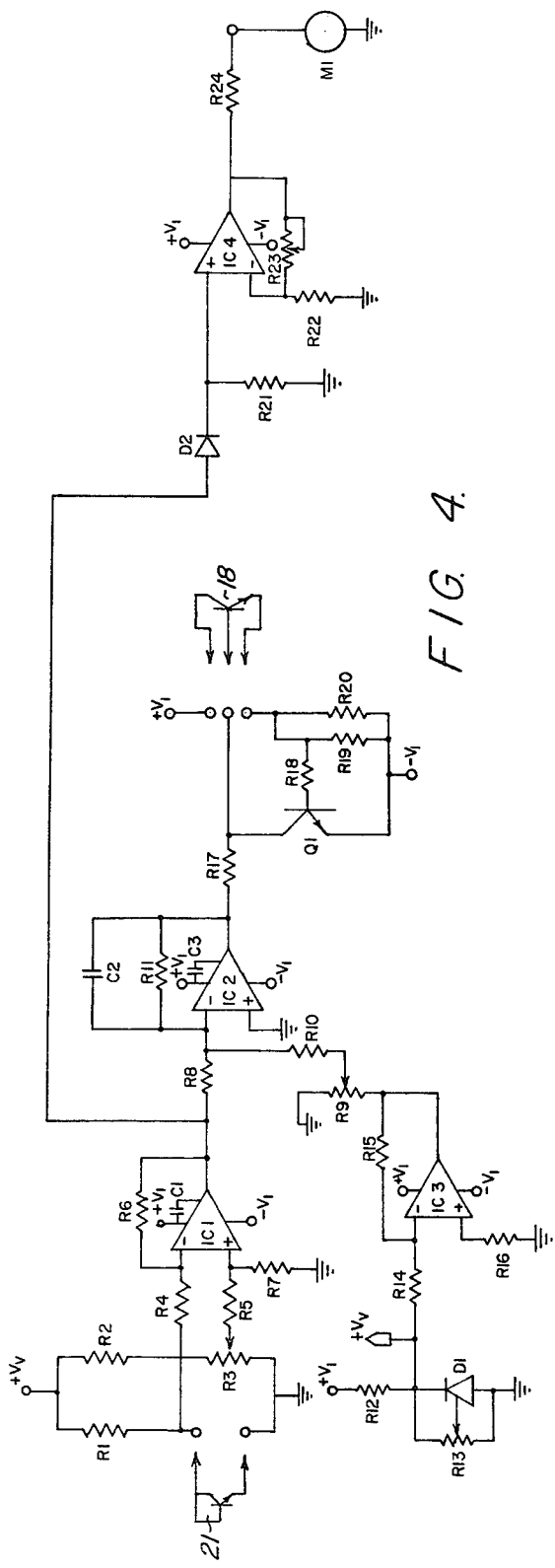

Typical heat sensing and heater control circuitry for cup 10 is illustrated in the circuit diagram of FIG. 4. Temperature sensing transistor 21 has its base and collector terminals connected together as shown in FIG. 2 to form a single terminal, which is connected to conductor 16. The emitter terminal is connected to conductor 17.

The RCA commercial transistor previously mentioned as SK3137 has a temperature coefficient of $-2$ mv/C°. It is connected as one leg of a Wheatstone bridge circuit, which includes resistors R1 and R2, FIG. 4, and the fixed resistance portion of variable resistor R3. The bridge is connected between a fixed voltage $+Vv$ and the circuit ground. One output of the bridge circuit is taken between resistor R1 and the temperature sensor and the other output is taken from the wiper of variable resistor R3. The outputs of the bridge circuit are connected to the inputs of an operational amplifier IC1, such as a National Semiconductor LH0044, which is connected in the normal manner with resistors R4 through R7 as a differential amplifier. Capacitor C1 is provided to stabilize IC1. Variable resistor R3 is adjusted so that the voltage on its wiper when the temperature sensor is at a temperature of 0° C. is equal to the voltage across the temperature sensor. Thus, at 0° C., the output of both branches of the bridge being equal, the differential amplifier IC3 has a 0 output. At any temperature other than 0° C. the inputs to the differential amplifier will be unequal and the amplifier will have an output.

The output of differential amplifier IC1 is connected through resistor R8 to the negative input terminal of operational amplifier IC2, which may also be a National Semiconductor LH0044. The wiper of variable resistor R9 is also connected, through resistor R10, to the negative input terminal of IC2 to create a reference voltage that is summed with the output voltage of IC2. The reference voltage is adjusted so that it is equal to but opposite in sign from the voltage generated by the differential amplifier IC1 at a certain temperature, for example 40° C., so that amplifier IC2 produces a 0 output at that certain temperature. For example, if the output of IC1 is 800 millivolts at 40° C., the reference voltage is adjusted to be equal to minus 800 millivolts. The output of IC2 is then 0 at a sensed temperature of 40° C. The desired temperature for 0 output of IC2 will usually be the desired temperature of the cup.

Resistor R11 and capacitor C2 are connected with respect to IC2 in standard fashion to stabilize the amplifier and give the desired gain. Capacitor C3 is provided to stabilize IC2. The amplifier is connected so that the output is of opposite sign from the input. Thus, if the sensed temperature is less than the desired temperature for which the reference voltage has been set, the input to the IC2 will be negative and the output will be a positive voltage. If the sensed temperature is greater than the desired temperature, the input to IC2 will be positive and the output will be a negative voltage.

The voltage across the fixed portion of variable resistor R9, which gives the range through which the reference voltage on the input of IC2 can be adjusted, may be obtained in any manner such as by connecting R9 directly across a voltage from a power supply. It is preferred, however, that the voltage across R9 be approximately $-1$ volt, so that a fine adjustment of the reference voltage within the range of 0 to $-1$ volt can be made. For this purpose, a voltage Vr of approximately 2.5 volts is obtained across an adjustable reference D1, such as a National Semiconductor LM336, which is connected in series with R12 across a positive voltage V1 from a power supply. Variable resistor R13 is used to adjust the voltage produced across the adjustable reference. This positive voltage $+Vr$, which may conveniently be used also as the voltage across the bridge circuit, is connected to an operational amplifier IC3 such as a Raytheon RC4132. Resistors R14 and R15 are arranged such that the output of IC3 is minus 1 volt. This, then, is the voltage which appears across the fixed portion of variable resistor R9. R16 stabilizes the $-1$ volt output of IC3 with respect to ambient temperature changes.

The output of IC2 is connected through resistor R17 to the base of heater transistor 18 attached to the cup. The collector of such heater transistor is connected to a source of positive voltage $+V1$, and the emitter is connected through a current limiting circuit (comprising a transistor Q1, such as a standard type 2N2222, and resistors R18, R19, and R20) to a source of negative voltage $-V1$. The purpose of the current limiting circuit is to allow only a maximum current of 400 milliamps to flow through heater transistor 18, so that the cup is heated slowly and a large overshoot in temperature does not occur. For example, if the cup is at a very low temperature and the current through the heater transistor is not limited, a very large initial current flows and causes very rapid heating of the cup. By the time the desired temperature is sensed and transistor 18 shut off, the residual heat in the transistor would cause the cup to reach a temperature of several degrees above the desired temperature. With the current limited, such overshoot does not occur and more accurate control upon initial heating of the cup is obtained.

When the output of IC2 is 0, indicating that the cup is at the proper temperature, the heater transistor circuitry is arranged so that a small current flows through transistor 18, thereby causing the transistor to generate enough heat to maintain the cup at the required temperature. This is because the 0 output of the amplifier that is connected to the base of heater transistor 18 is compared to negative voltage $-V1$, which is connected through the current-limiting circuitry to the emitter of heater transistor 18. This arrangement provides a bias of approximately +1.8 volts on the base of heater transistor 18 when −V1 is −3 volts. If the temperature of the cup rises above the desired temperature, as mentioned above, the output of IC2 becomes negative. This decreases the bias on the base of heater transistor 18 and decreases current flow through such transistor and the heat generated by it. This allows cup 10 to cool. On the other hand, if cup temperature falls below the desired temperature, the output of IC2 becomes positive. This increases the bias on the base of heater transistor 18, causing more current to flow through such transistor to generate additional heat, which is transferred to cup 10.

In many instances, it is desirable to monitor the temperature of cup 10 by providing a visual read-out means, such as a meter calibrated in temperature units so as to indicate the temperature of the cup. For this purpose, the output of IC1 (which is an indication of the temperature sensed by temperature sensing transistor 21) is connected to a meter-driving circuit comprising diode D2, resistors R21 through R24, and operational amplifier IC4. The latter may be a National Semiconductor LM741.

Diode D2 is used to block the voltage from IC1 until it reaches the level to place the diode in its conducting condition. This is at a voltage which represents approximately 30° C. In this way, there is no meter reading for temperatures below 30° C. A diode of the Fairchild IN457 type has been found satisfactory as diode D2 for this purpose. The voltage passed by D2 enters operational amplifier IC4 with its associated resistors R21, R22, R23, and R24, which produces an output to drive a meter, such as a 0–10 milliamp meter calibrated in terms of temperature.

Variable resistor R23 may be used to calibrate the meter. With diode D2, the meter may be calibrated for a reading over its full scale, indicating temperatures between 30° C. and an upper limit, such as 50° C. If it is desired to read temperatures over a larger range, diode D2 may be elminated, thereby providing meter readings ranging from 0° C. upwardly. It should be noted that the meter circuitry provides the current necessary for driving the meter without loading differential amplifier IC1.

While any type of power supply may be used to provide the power for the circuitry and transistors described, it is preferred for safety reasons and to provide portability for the unit that the power source be a 6 volt battery. A satisfactory power supply for the circuitry illustrated is shown in FIG. 5.

Figure 5:
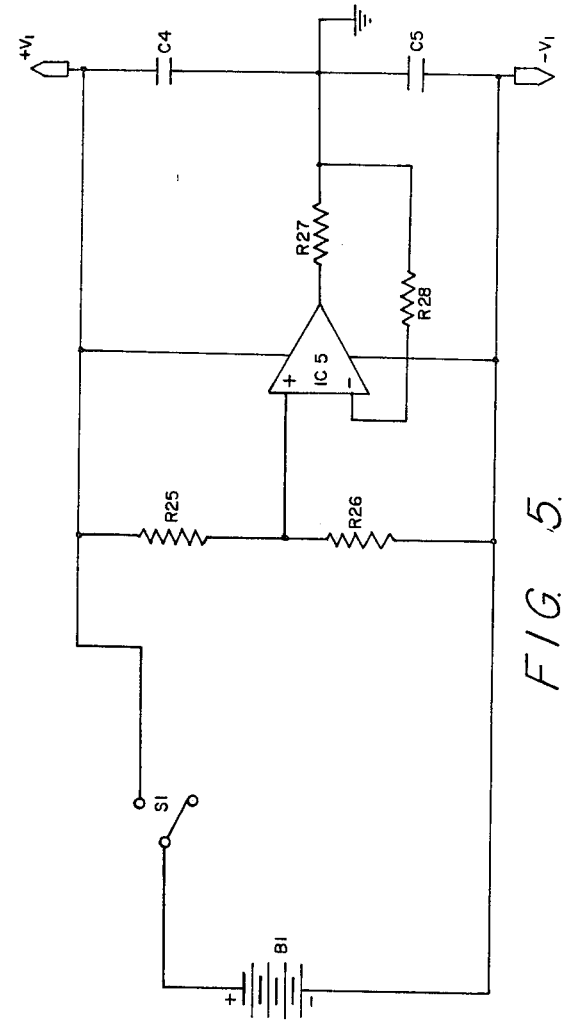

In the power supply of FIG. 5, a 6 volt, rechargeable battery B1, such as a Gould Gel Cell, is provided as a power source. Its positive terminal is connected, through switch S1, to a terminal labeled +V1. Its negative terminal is connected to a terminal labeled −V1. Resistors R25 and R26, both of equal resistance, are connected in series between +V1 and −V1 to form a voltage divider producing a voltage at their junction of one-half the voltage difference between +V1 and −V1, or 3 volts. The voltage of the junction of resistors R25 and R26 is an input to an operational amplifier IC5, such as a Raytheon RC4132, which is arranged with resistors R27 and R28 to provide unity gain and create the common or ground point for the circuitry, which will remain at a voltage exactly halfway between +V1 and −V1. The purpose of IC5 is to provide a current source and isolate resistors R25 and R26, so that changes in current flow in various parts of the circuitry do not cause changes in voltage across either R25 or R26. Such changes in voltage would be undesirable, because they would cause the value of the divided voltage to vary from a value exactly halfway between +V1 and −V1.

The output of IC5 is connected through capacitors C4 and C5 to terminals +V1 and −V1 and forms the common or ground terminal of the circuitry. In this way the ground for the circuitry always remains at one-half the difference between +V1 and −V1, and, therefore, with the 6 volt battery, +V1 is always plus 3 volts and −V1 is always minus 3 volts with respect to the common or ground terminal.

As previously indicated, it is preferable that the battery be of rechargeable type and that the unit include a charger for the battery. The charger may be of any standard type for use with 6 volt batteries and preferably contains circuitry to protect against overcharging. The circuitry may also contain an indicator to show when the battery is in need of being charged.

Although it is desirable that the heated cup and its associated circuitry be a completely separate and independent unit, the cup heat sensing and heater control circuitry may be combined with iontophoresis circuitry as used to induce sweating in a patient to be tested. Thus, the power supply circuitry and possibly other portions of the iontophoresis circuitry could be in common with the heat sensing and heater control circuitry.

With the cup device of this invention, it is possible to set a temperature slightly above skin temperature such as 40° C., so as to be comfortable but preventing condensate from forming in the cup, which would lead to errors in evaluation of the sweat. The length of the sweat collection time is not critical, because the cup may be maintained at the desired temperature indefinitely. Thus, if a sweat collection time of over the customary 15 minutes is necessary to collect the required amounts of sweat for analysis, it presents no problem.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:
1. For use in combination with equipment for inducing sweat from humans, a sweat collection device, comprising a thermally conductive cup having a flat bottom; an electric heating element attached to the cup bottom flatwise exteriorly of the cup; electrical means for energizing the heating element; a temperature sensor positioned on the flat bottom of the cup and arranged to monitor the temperature of the cup; a thermally conductive pad positioned between the heating element and the flat bottom of the cup; mechanical means clamping the heating element against said pad; and means electrically connected between the temperature sensor and the means for energizing the heating element so that the temperature of the cup is maintained at a constant preset temperature.

2. A device according to claim 1, wherein the bottom of the cup and the structure mounted thereon are covered by an insulating boot.

3. A device according to claim 1, wherein the heating element is a transistor.

4. A device according to claim 2, wherein the means for energizing the heating element so that the temperature of the cup is maintained at a constant preset temperature includes means for controlling the bias on the base of the transistor.

5. A device according to claim 4, wherein the temperature sensor is also a transistor, such sensor transistor having base and collector connected as a common terminal.

6. A device according to claim 5, wherein the temperature sensor forms one element of a Wheatstone bridge circuit, the output of the bridge circuit being an indication of the temperature of the cup and controlling the bias on the base of the heating transistor.

7. A device according to claim 1, wherein the temperature sensor is also a transistor, such sensor transistor having base and collector connected as a common terminal.

8. In the medical evaluation of human sweat, which includes collecting sweat from a medical patient by heated cup and removing all or portions of the collected sweat from the cup for analysis, the improvement comprising electrically heating the collection cup as may be required to maintain said collection cup at a substantially constant temperature at and during the time of collection of the sweat sample, said substantially uniform temperature being equal to or greater than the temperature of the skin from which the sample is being collected; continually monitoring the temperature of the cup to determine when and the degree of heat to be added to the cup and to determine when adding of heat is to be discontinued; and controlling the supply of electrical power to the cup in accordance with heat requirements determined by said temperature monitoring.

* * * * *